(12) United States Patent
Jennings

(10) Patent No.: US 10,660,983 B2
(45) Date of Patent: May 26, 2020

(54) HAND SANITIZING STATION

(71) Applicant: Audrey Jean Jennings, Chicago, IL (US)

(72) Inventor: Audrey Jean Jennings, Chicago, IL (US)

( * ) Notice: Subject to any disclaimer, the term of this patent is extended or adjusted under 35 U.S.C. 154(b) by 0 days.

(21) Appl. No.: 16/101,989

(22) Filed: Aug. 13, 2018

(65) Prior Publication Data
US 2019/0001009 A1    Jan. 3, 2019

Related U.S. Application Data

(63) Continuation-in-part of application No. 15/599,439, filed on May 18, 2017, now abandoned.

(51) Int. Cl.
| | | |
|---|---|---|
| *A61L 2/26* | (2006.01) | |
| *A61L 2/00* | (2006.01) | |
| *A45D 34/00* | (2006.01) | |
| *A61L 2/18* | (2006.01) | |
| *A61L 2/22* | (2006.01) | |
| *B65D 35/28* | (2006.01) | |
| *A47K 10/42* | (2006.01) | |
| *A47K 5/12* | (2006.01) | |
| *B05B 11/00* | (2006.01) | |
| *A47K 5/18* | (2006.01) | |
| *A47K 10/38* | (2006.01) | |

(52) U.S. Cl.
CPC ............... *A61L 2/26* (2013.01); *A45D 34/00* (2013.01); *A47K 5/12* (2013.01); *A47K 5/1202* (2013.01); *A47K 5/1217* (2013.01); *A47K 10/422* (2013.01); *A47K 10/427* (2013.01); *A61L 2/0088* (2013.01); *A61L 2/18* (2013.01); *A61L 2/22* (2013.01); *B05B 11/00* (2013.01); *B65D 35/28* (2013.01); *A45D 2200/054* (2013.01); *A47K 5/18* (2013.01); *A47K 2010/389* (2013.01); *A61L 2202/14* (2013.01); *A61L 2202/15* (2013.01); *A61L 2202/21* (2013.01)

(58) Field of Classification Search
CPC ..... A61L 2/26; A61L 2/18; A61L 2/22; A61L 2202/14; A61L 2202/15; A61L 2202/21; B65D 35/28
USPC ............... 221/33, 4; 198/471.1, 397; 452/31
See application file for complete search history.

(56) References Cited

U.S. PATENT DOCUMENTS

| 1,103,225 | A | * | 7/1914 | Schindeler | ............. | A47B 67/04 |
| | | | | | | 312/287 |
| 2,540,930 | A | * | 2/1951 | Campbell | ............... | A47K 10/44 |
| | | | | | | 221/228 |
| 3,854,624 | A | * | 12/1974 | Canci | ..................... | A47G 19/32 |
| | | | | | | 221/96 |
| 3,865,271 | A | * | 2/1975 | Gold | ...................... | A47K 10/32 |
| | | | | | | 221/96 |

(Continued)

*Primary Examiner* — Rakesh Kumar
(74) *Attorney, Agent, or Firm* — McAndrews, Held & Malloy, Ltd.

(57) ABSTRACT

An apparatus for sanitizing hands comprising a base, wherein the base is configured to dispense towels; at least one dispensing chamber configured to store a viscous material comprising a conduit; at least one sensor activated pump mechanism comprising a sensor device connected to a circuit system, an actuator, and an energy source; and wherein when the sensor device is triggered, the sensor activated pump mechanism is configured to draw a predetermined volume of viscous material through the conduit and out the discharge nozzle.

9 Claims, 8 Drawing Sheets

(56) References Cited

U.S. PATENT DOCUMENTS

| | | | | |
|---|---|---|---|---|
| 4,667,846 A * | 5/1987 | Marceau | A47K 10/32 |
| | | | 221/34 |
| 5,690,255 A * | 11/1997 | White | A47B 77/00 |
| | | | 222/135 |
| 6,530,502 B2 * | 3/2003 | Neal | A47L 17/00 |
| | | | 222/108 |
| 7,497,351 B2 * | 3/2009 | Amundson | A47K 10/421 |
| | | | 221/135 |
| 8,087,543 B2 * | 1/2012 | Yang | A47K 5/1217 |
| | | | 222/52 |
| 8,109,411 B2 * | 2/2012 | Yang | G01F 13/006 |
| | | | 222/52 |
| 9,265,383 B2 * | 2/2016 | Yang | A47K 5/1217 |
| 9,763,546 B2 * | 9/2017 | Yang | A47K 5/1217 |
| 9,770,308 B2 * | 9/2017 | Fern | A61B 90/00 |
| 9,884,336 B2 * | 2/2018 | Hoefte | A47K 5/12 |
| 2002/0040912 A1 * | 4/2002 | McHugh | A61B 50/20 |
| | | | 221/45 |
| 2004/0226962 A1 * | 11/2004 | Mazursky | A47K 5/1217 |
| | | | 222/95 |
| 2008/0185399 A1 * | 8/2008 | Yang | A47K 5/1217 |
| | | | 222/52 |
| 2009/0212072 A1 * | 8/2009 | Fenton | B05B 11/0054 |
| | | | 222/173 |
| 2019/0001009 A1 * | 1/2019 | Jennings | A47K 5/1217 |

* cited by examiner

US 10,660,983 B2

HAND SANITIZING STATION

RELATED APPLICATIONS

The present patent application is a continuation-in-part of U.S. patent application Ser. No. 15/599,439, filed May 18, 2017 and claims the priority benefit of the aforementioned application. The content of the aforementioned application is hereby incorporated by reference in its entirety into this disclosure.

FEDERALLY SPONSORED RESEARCH OR DEVELOPMENT

[Not Applicable]

FIELD OF THE INVENTION

The present invention generally relates to a hand washing station comprising of at least two dispensers for liquid soap or other viscous materials and a paper towel holder.

BACKGROUND OF THE INVENTION

People are getting caught dirty-handed when it comes to their hand washing habits. While individuals understand the importance of hand hygiene, actual practices don't reflect that. A study of college students found that female students washed their hands 76% of the time, while their male peers admitted to washing their hands only 57% of the time. Anderson, J. L., Warren, C. A., Perez, E., Louis, R. I., Phillips, S., Wheeler, J., & Misra, R. (2008). Gender and ethnic differences in hand hygiene practices among college students. *American Journal of Infection Control*, 36(5), 361-368. doi:10.1016/j.ajic.2007.09.007. One study has shown that "[a]bout 7% of the women and 14.6% of the men did not wash their hands at all, while 15.1% of the women and 35.1% of the men simply wet their hands with water." Borchgrevink, C. P., Cha, J., & Kim, S. (2013). Hand washing practices in a college town environment. *Journal of Environmental Health*, 75(8), 18-24.

Research has found that hand washing is an easy, inexpensive, and effective way to prevent the spread of germs and keep people healthy. Not only people, but it also prevents cross-contamination of food in the home as well as in our food processing facilities. Handwashing: Clean Hands Save Lives. (2017 Dec. 8). Retrieved from https://www.cdc.gov/handwashing/index.html Typically soap dispensers are either wall-mounted our counter-mounted. Wall-mounted soap dispensers require a support base which is attached to a wall. The liquid soap, or other viscous material, usually comes with a feeding tube which is placed on a holding base that is typically present on the support base. A cover usually attaches to the support base to close up the liquid soap or other viscous material. Counter-mounted dispensers require a cutout within the sink. Typically these dispensers require screwing the pump onto a soap reservoir which can be messy.

Many of these dispensers are manual, requiring a user to press a lever or pump top, potentially spreading dangerous germs and bacteria. In some instances the dispenser is automatic, but these still suffer from clogging and may be placed far from the sinks and or hand drying stations, contributing to the presence of standing water. Additionally, counter-mounted dispensers typically have low volume reservoirs which require constant filling.

Studies have found that in some situations hand sanitizer use results in a greater reduction of *E. coli* and fecal streptococci when compared to hand washing. Pickering, A. J., Boehm, A. B., Mwanjali, M., & Davis, J. (2010). Efficacy of Waterless Hand Hygiene Compared with Handwashing with Soap: A Field Study in Dar es Salaam, Tanzania. *American Journal of Tropical Medicine and Hygiene*, 82(2), 270-278. doi:10.4269/ajtmh.2010.09-0220. However, most hand commercial or public hand washing stations do not have hand sanitizer near the soap dispensers.

Drying hand using an air dryer can also contribute to bacterial contamination as compared to using towels to dry hand. One study discovered that "[j]et air and warm air dryers result in increased bacterial aerosolization when drying hands. These results suggest that air dryers may be unsuitable for use in healthcare settings, as they may facilitate microbial cross-contamination via airborne dissemination to the environment or bathroom visitors." Best, E., Parnell, P., & Wilcox, M. (2014). Microbiological comparison of hand-drying methods: The potential for contamination of the environment, user, and bystander. *Journal of Hospital Infection*, 88(4), 199-206. doi:10.1016/j.jhinches2014.08.002. Furthermore, it's has been discovered that show bottoms "had the highest [percentage] of positive samples [of *Clostridium difficile* . . . the leading cause of infectious diarrhea in hospitalized adults]." Alam, M. J., Anu, A., Walk, S. T., & Garey, K. W. (2014). Investigation of potentially pathogenic *Clostridium difficile* contamination in household environs. Anaerobe, 27, 31-33. doi: 10.1016/j.anaerobe.2014.03.002.

In most public and commercial facilities, hand dryers or paper towel dispensers are wall-mounted in the bathroom facilities. Not only do these dryers take up additional space, but their typical low drying speed also requires a user to stand for prolonged periods of time in front of the hand dryer, potentially spreading dangerous germs and bacteria. Additionally, since most hand dryers or paper towel dispensers are away from the hand washing stations, a user has to walk away from the sink with wet hands, dripping soap and water. Even when the hand dryers are near the hand washing stations, the forceful air can blow dangerous germs and bacteria into the air if the user has not properly washed their hands.

In order to keep hands sanitary, there exists a need for a streamlined hand cleaning, drying, and sanitizing station that can be placed near a faucet, which is light and compact enough to be portable.

BRIEF SUMMARY OF THE INVENTION

In at least one aspect, the present technology provides at least one apparatus for sanitizing hands comprising a base, wherein the base is configured to dispense towels; wherein the base comprises a bottom wall, a back wall, at least one interior side wall, at least one exterior side wall, and a front wall; wherein the bottom wall includes a battery holder, switch, and a motor; at least one dispensing chamber configured to store a viscous material comprising a conduit; wherein the dispensing chamber is connected to the base using the conduit; at least one chamber cap placed on top of the at least one dispensing chamber comprising a discharge nozzle and a sliding portion, at least one sensor activated pump mechanism comprising a sensor device connected to a circuit system, an actuator, and an energy source; wherein when the sensor device is triggered, the sensor activated pump mechanism is configured to draw a predetermined volume of viscous material through the conduit and out the discharge nozzle.

The unique configuration of the present technology provides a space saving design for easy and convenient access to hand cleansing agents and reduction of standing water. Additionally, since the energy source is housed within the base, a user can switch the dispensing chambers. For example, in an aspect of the invention where there are two dispensing chambers, one dispensing chamber can be made from plastic while the other is made from stainless steel. This unique configuration allows a user to customize the present technology in new and unexpected manners.

In some aspects, the viscous material is selected from the group consisting of soap, lotion, hand sanitizer, essential oil, foam, gel, shampoo, conditioner, topical medication, liquid baby powder, dye, hair mousse, toothpaste, mouthwash, liquid makeup, facial creams, sunscreen, detergent, and shaving cream.

In some aspects, the sliding portion is configured to allow a user to select a predetermined volume of viscous material to be dispensed.

In some aspects, the chamber cap may be configured to form a seal at the top of the dispensing chamber for maintaining the viscous material within the dispensing chamber.

In yet another aspect, the apparatus includes a compartment cover placed over the chamber cap that comprises a refill cap opening and refill cap, wherein the refill cap can be lifted to refill the dispensing chamber with a viscous material.

In some aspects, the circuit system is selected from the group consisting of a circuit board, integrated circuit, or circuitry device. In some aspects, the circuit system has preset input that can switch the output of the energy source to provide operational power to the actuator when the sensor device is triggered.

In some aspects, the actuator is an electric motor. In another aspect, the sensor device is an infrared sensor. In an additional aspect, the energy source is a battery. In yet a further aspect, the battery is selected from a group consisting of nickel-metal-hydride batteries or lithium ion batteries.

In some aspects, the base is configured to store a plurality of towels. In another aspect, the towels are stored in the base in an interleaved manner or as a continuous roll. In yet another aspect, the base comprises a spring mechanism for dispensing the plurality of towels one by one.

In some aspects, the at least one dispensing chamber is made from a material selected from the group consisting of vinyl, plastic, plastic polymers, copper, pewter, and stainless steel. In another aspect, the plastic polymers are selected from the group consisting of consisting of low-density polyethylene, high-density polyethylene, polypropylene, polyvinyl chloride, polystyrene, nylon, polytetrafluoroethylene, and thermoplastic polyurethanes. In yet another aspect, the at least one dispensing chamber further comprises a back wall formed of a transparent material.

In some aspects, the front wall includes a cutout extending no more than 3 inches from the top of the front wall. In some aspects, the conduit is covered by a conduit cover.

In some aspects, there is at least two sensor activated pump mechanisms. In yet another aspect, the sensor activated pump mechanisms are independently powered by separate energy sources. In yet a further aspect, the sensor activated pump mechanisms triggered by the actuator to dispense a predetermined quantity of viscous material.

In at least one aspect, the present technology provides at least one apparatus for sanitizing hands comprising a base, wherein the base is configured to dispense towels; wherein the base includes a bottom wall, a back wall, at least one interior side wall, at least one exterior side wall, and a front wall; wherein the bottom wall includes a battery holder, switch, and a motor connected using electrical wiring; at least one dispensing chamber comprising a conduit, wherein the dispensing chamber is configured to store a viscous material; wherein the dispensing chamber is connected to the base via the conduit; wherein the viscous material is selected from the group consisting of soap, lotion, hand sanitizer, essential oil, foam, gel, shampoo, conditioner, topical medication, liquid baby powder, dye, hair mousse, toothpaste, mouthwash, liquid makeup, facial creams, sunscreen, detergent, and shaving cream; at least one chamber cap comprising a discharge nozzle and a sliding portion, wherein the sliding portion allows a user to select a predetermined volume of viscous material; wherein the chamber cap may be configured to form a seal at the top of the dispensing chamber for maintaining the viscous liquid within the dispensing chamber; at least one sensor activated pump mechanism consisting of a sensor device, an actuator, and an energy source; wherein when the sensor device is triggered, the sensor activated pump mechanism is configured to draw a predetermined volume of viscous material through the conduit and out the discharge nozzle; wherein the sensor device is connected to a circuit system such as a circuit board, integrated circuit, or circuitry device; and a compartment cover placed over the chamber cap that comprises a refill cap opening and refill cap that can be lifted to refill the dispensing chamber.

In at least one aspect, the present technology provides at least one apparatus for sanitizing hands comprising a base, wherein the base is configured to dispense towels; wherein the base includes a bottom wall, a back wall, at least one interior side wall, at least one exterior side wall, and a front wall; wherein the front wall includes a cutout extending no more than 3 inches from the top of the front wall; wherein the bottom wall includes a battery holder, switch, and a motor connected using electrical wiring; at least one dispensing chamber comprising a conduit, wherein the dispensing chamber is configured to store a viscous material; wherein the dispensing chamber is connected to the base via the conduit; wherein the conduit is covered by a conduit cover; wherein the viscous material is selected from the group consisting of soap, lotion, hand sanitizer, essential oil, foam, gel, shampoo, conditioner, topical medication, liquid baby powder, dye, hair mousse, toothpaste, mouthwash, liquid makeup, facial creams, sunscreen, detergent, and shaving cream; wherein the dispensing chamber is made from vinyl, plastic, plastic polymers like low-density polyethylene, high-density polyethylene, polypropylene, polyvinyl chloride, polystyrene, nylon, polytetrafluoroethylene, and thermoplastic polyurethanes, copper, pewter, stainless steel; wherein the dispensing chamber has at least a transparent backing; at least one chamber cap comprising a discharge nozzle placed at the edge of the chamber cap and a sliding portion, wherein the sliding portion allows a user to select a predetermined volume of viscous material; wherein the chamber cap may be configured to form a seal at the top of the dispensing chamber for maintaining the viscous liquid within the dispensing chamber; at least one sensor activated pump mechanism consisting of a sensor device, an actuator, and an energy source; wherein when the sensor device is triggered, the sensor activated pump mechanism is configured to draw a predetermined volume of viscous material through the conduit and out the discharge nozzle; wherein the sensor device is connected to a circuit system such as a circuit board, integrated circuit, or circuitry device; and a compartment cover placed over the chamber cap that comprises a refill cap opening and refill cap that can be lifted to refill the dispensing chamber.

Some aspects further comprise an opening on the chamber cap where the viscous material can be poured into the dispensing chamber.

In at least one aspect, the present technology provides at least one apparatus for sanitizing hands comprising a base configured to dispense towels comprising a bottom wall, a back wall, at least one interior side wall, at least one exterior side wall, and a front wall; wherein the back wall comprises a latch hook for loading towels into the base; wherein the bottom wall includes a battery holder, switch, and a motor; two dispensing chambers configured to store a viscous material, each dispensing chamber comprising a conduit; wherein each dispensing chamber is connected to opposite sides of the base using the conduit; two chamber caps placed on top of each dispensing chamber, each chamber cap comprising a discharge nozzle placed at the edge of the chamber cap, an opening for the viscous material to be poured into the dispensing chamber, and a sliding portion, wherein the sliding portion allows a user to select a predetermined volume of viscous material; two sensor activated pump mechanisms each consisting of a sensor device, an actuator, and an energy source; wherein when the sensor device is triggered, the sensor activated pump mechanism is configured to draw a predetermined volume of viscous material through the conduit and out the discharge nozzle; wherein the sensor activated pump mechanisms are independently powered by separate energy sources and triggered by the actuator to dispense a predetermined quantity of viscous material.

DETAILED DESCRIPTION OF THE INVENTION

It is to be understood by one of ordinary skill in the art that the present discussion is a description of exemplary embodiments only, and is not intended as limiting the broader aspects of the present invention, which broader aspects are embodied in the exemplary constructions.

The present technology provides at least one apparatus for use in washing and/or sanitizing the hands of a user.

Figure 1:
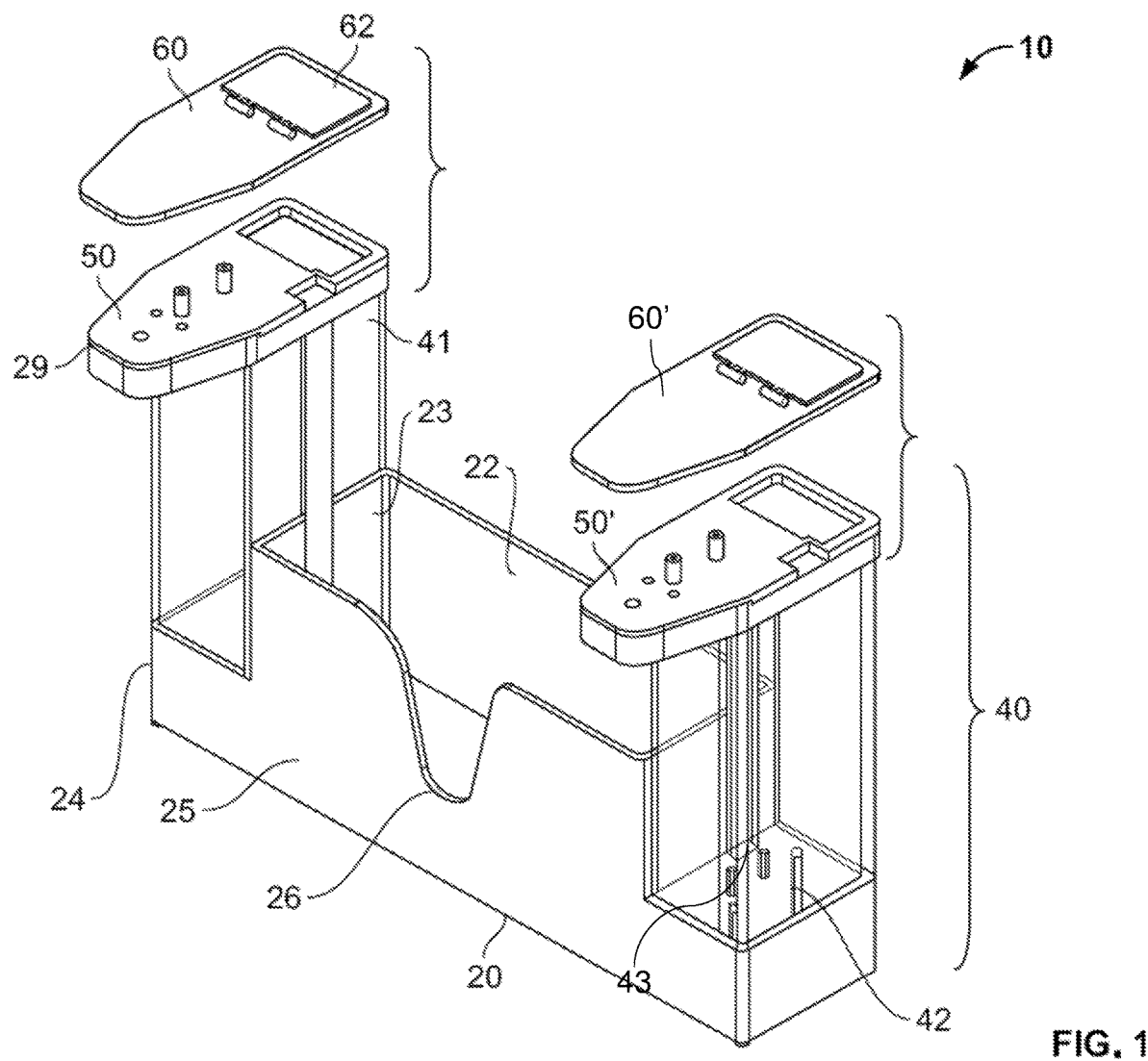
FIG. 1 illustrates a configuration of a hand sanitizing station according to an aspect of the present invention as it may appear when placed on a counter or other horizontal surface.

FIG. 1 illustrates the configuration of a hand sanitizing station 10 according to an aspect of the present invention as it may appear when placed on a counter or other horizontal surface.

Figure 2:
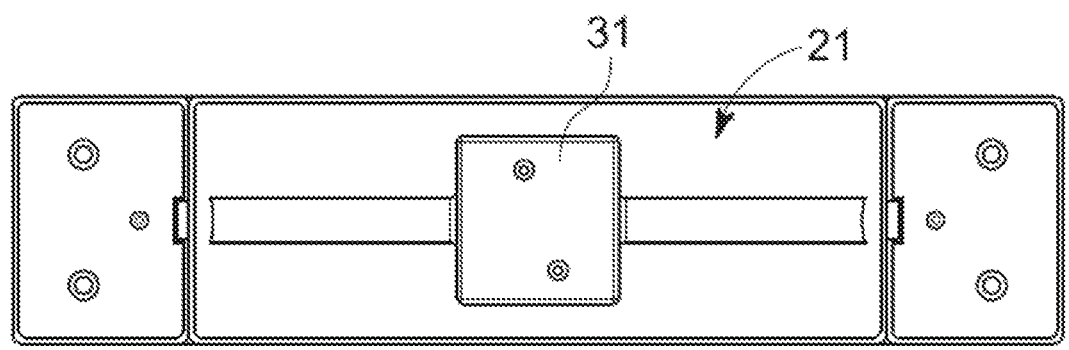
FIG. 2 illustrates a bottom perspective view of a base of the hand sanitizing station.
Figure 3:
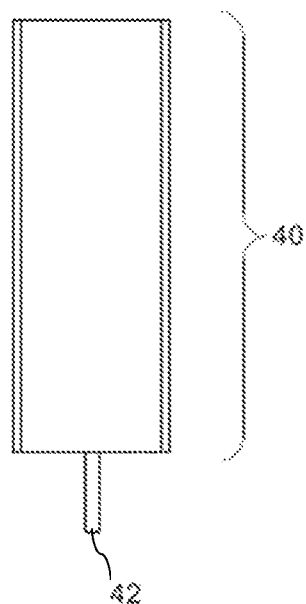
FIG. 3 Illustrates a side perspective view of a dispensing chamber.

As illustrated in FIGS. 1 and 2, the hand sanitizing station 10 includes a base 20. The base 20 can take any shape but in the illustrated embodiment the base 20 has a substantially rectangular shape. However, in other non-illustrated embodiments, the base 20 may comprise different shapes to produce a different aesthetic. The base 20 may include a bottom wall 21, a back wall 22, at least one interior side wall 23, at least one exterior side wall 24, and a front wall 25. In some embodiments, the bottom wall 21 is no more than about 15 inches long and no more than about 4 in wide. In some embodiments, the back wall 22 is no more than about 15 inches long and no more than about 6 in high. In some embodiments, the interior side wall 23 is no more than about 6 inches high. In some embodiments, the exterior side wall 24 is no more than about 3 inches high. In some embodiments, the front wall 25 is no more than about 15 inches long and no more than about 6 in high.

In some embodiments, the front wall 25 also includes a cutout 26. The cutout 26 can take any shape, but in the illustrated embodiment, the cutout 26 has a substantially u-shape. However, in other non-illustrated embodiments, the cutout 26 may comprise different shapes to produce a different aesthetic. In some embodiments, the cut out 26 extends no more than about 3 inches from the top of the front wall 25.

In some embodiments, towels for drying are placed inside the base 20. In these embodiments, the cutout 26 allows a user to grab a towel for drying easily. In some aspects, the bottom wall 21 comprises a spring or similar device which pushes the towel for drying to the top of the base 20 so that a user does not need to reach far into the towel dispenser to dry their hands.

As illustrated in FIG. 2, the bottom wall 21 may include a battery holder 31, switch, and a motor. The battery holder 31, switch, and a motor are connected using electrical wiring.

The hand sanitizing station 10 includes at least one dispensing chamber 40. In the illustrated embodiment the hand sanitizing station 10 includes two dispensing chambers 40. The dispensing chamber 40 in the illustrated embodiment is configured to store a viscous material, such as soap, lotion, hand sanitizer, essential oil, foam, gel, shampoo, conditioner, topical medication, liquid baby powder, dye, hair mousse, toothpaste, mouthwash, liquid makeup, facial creams, sunscreen, detergent, and shaving cream.

Figure 7:
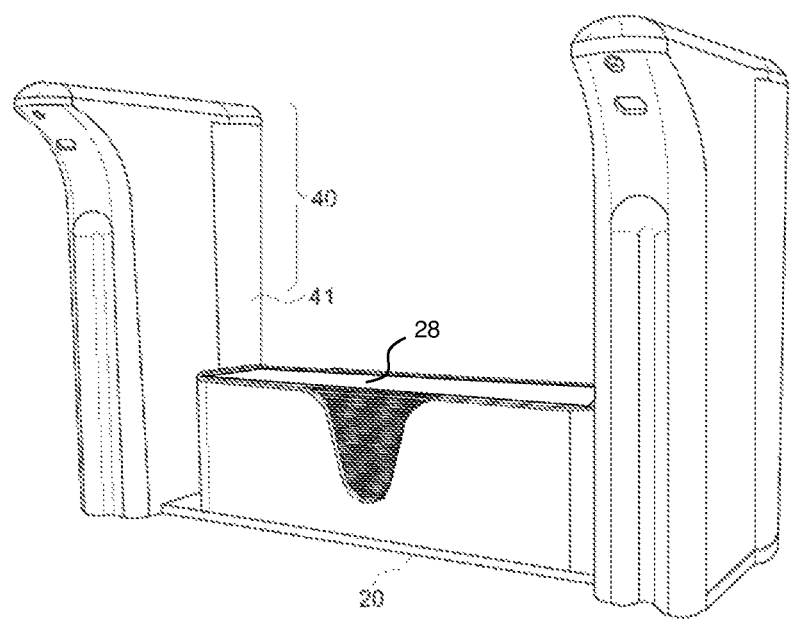
FIG. 7 illustrates a configuration of a hand sanitizing station according to an aspect of the present invention with a transparent back chamber wall.

The dispensing chamber 40 can be any type of container or made from any type of material. In some embodiments, the dispensing chamber is made from vinyl, plastic, plastic polymers like low-density polyethylene, high-density polyethylene, polypropylene, polyvinyl chloride, polystyrene, nylon, polytetrafluoroethylene, and thermoplastic polyurethanes, copper, pewter, stainless steel. In some embodiments, the dispensing chamber 40 is transparent. In other embodiments, as illustrated in FIG. 7, the dispensing chamber 40 includes a back wall 41 formed of a transparent material. In some embodiments, the dispensing chamber 40 is no more than about 3 in wide and no more than about 7 in tall. The dispensing chamber 40 is connected to the base 20 with a coupling conduit 42. Any type or diameter of conduit can be used. In some embodiments, the coupling conduit 42 is covered by a conduit cover.

As illustrated in FIG. 1, the hand sanitizing station may include two chamber caps 50, 50' and two compartment covers 60, 60'. The chamber cap 50 or caps 50, 50' may be configured to form a seal 29 at the top of the dispensing chamber 40 for maintaining the viscous liquid within the dispensing chamber 40.

Figures 4A, 4B:
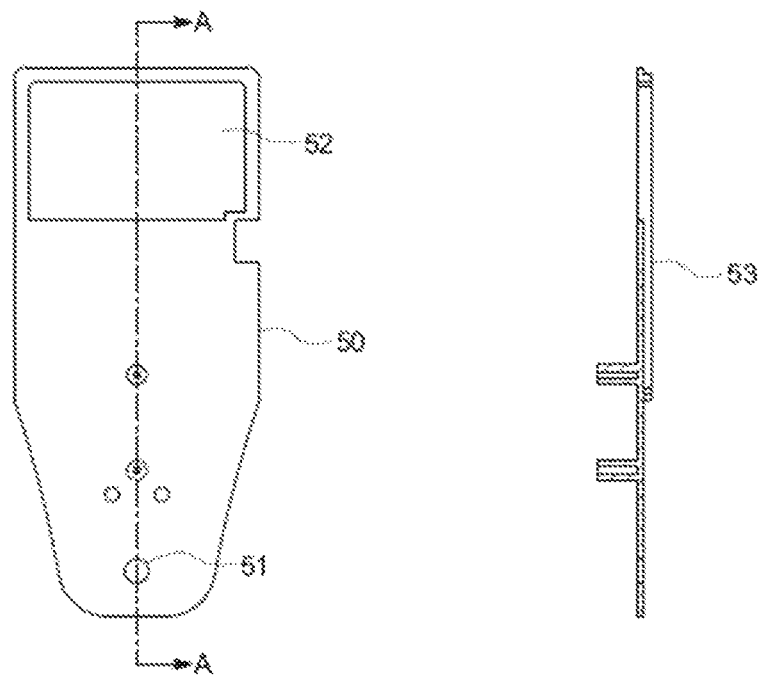
FIGS. 4A and 4B illustrate a top and side perspective view of a chamber cap.

As illustrated in FIG. 4A, the hand sanitizing station 10 includes at least one chamber cap 50. The chamber cap 50 may be configured to form a seal at the top of the dispensing chamber 40 for maintaining the viscous liquid within the dispensing chamber 40. The chamber cap 50 includes discharge nozzle 51. Any type of discharge nozzle can be used. In some embodiments, the discharge nozzle 51 is placed on the edge of the chamber cap 50 allowing a user to easily place their hands or another body part under the chamber cap 50 for easy dispensing of the viscous material. In some embodiments, the chamber cap 50 includes an opening 52 where the viscous material can be poured into the dispensing chamber. In some embodiments, as illustrated in FIG. 4B, the chamber cap 50 includes a sliding portion 53 which allows for a user to adjust the volume of viscous material dispensed. The sliding portion 53 may sit over the opening 52 of the chamber cap 50.

Figure 5A:
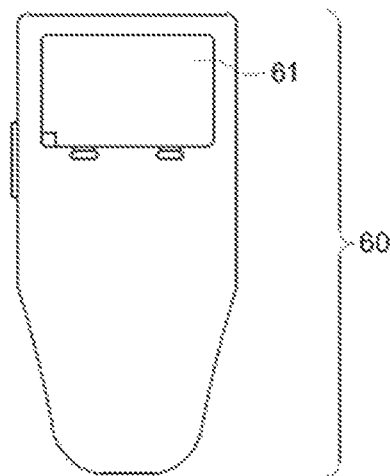
FIG. 5A illustrates a top perspective view of a compartment cover.
Figure 5B:
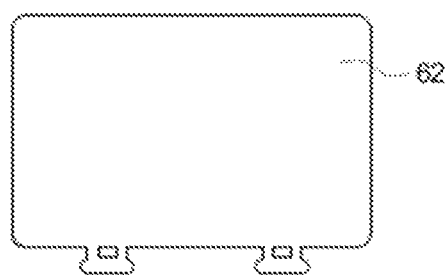
FIG. 5B illustrates a top perspective view of a refill cap.
Figure 5C:
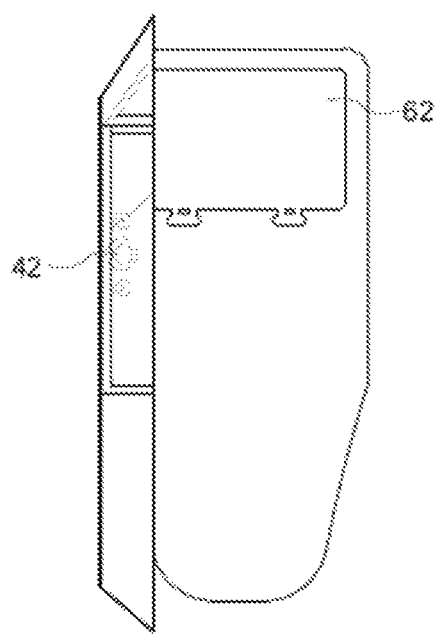
FIG. 5C illustrates a top perspective view of a compartment cover showing the refill cap attached and a conduit.

As illustrated in FIG. 5A, the hand sanitizing station 10 includes at least one compartment cover 60. The compartment cover 60 is placed over the chamber cap 50 covering the discharge nozzle 51 and sliding portion 53. The compartment cover 60 also includes a refill cap opening 61 and refill cap 62. The refill cap 62 can be lifted up to allow a user to refill the dispensing chamber 40 without the need to remove the chamber cap.

Figure 6A:
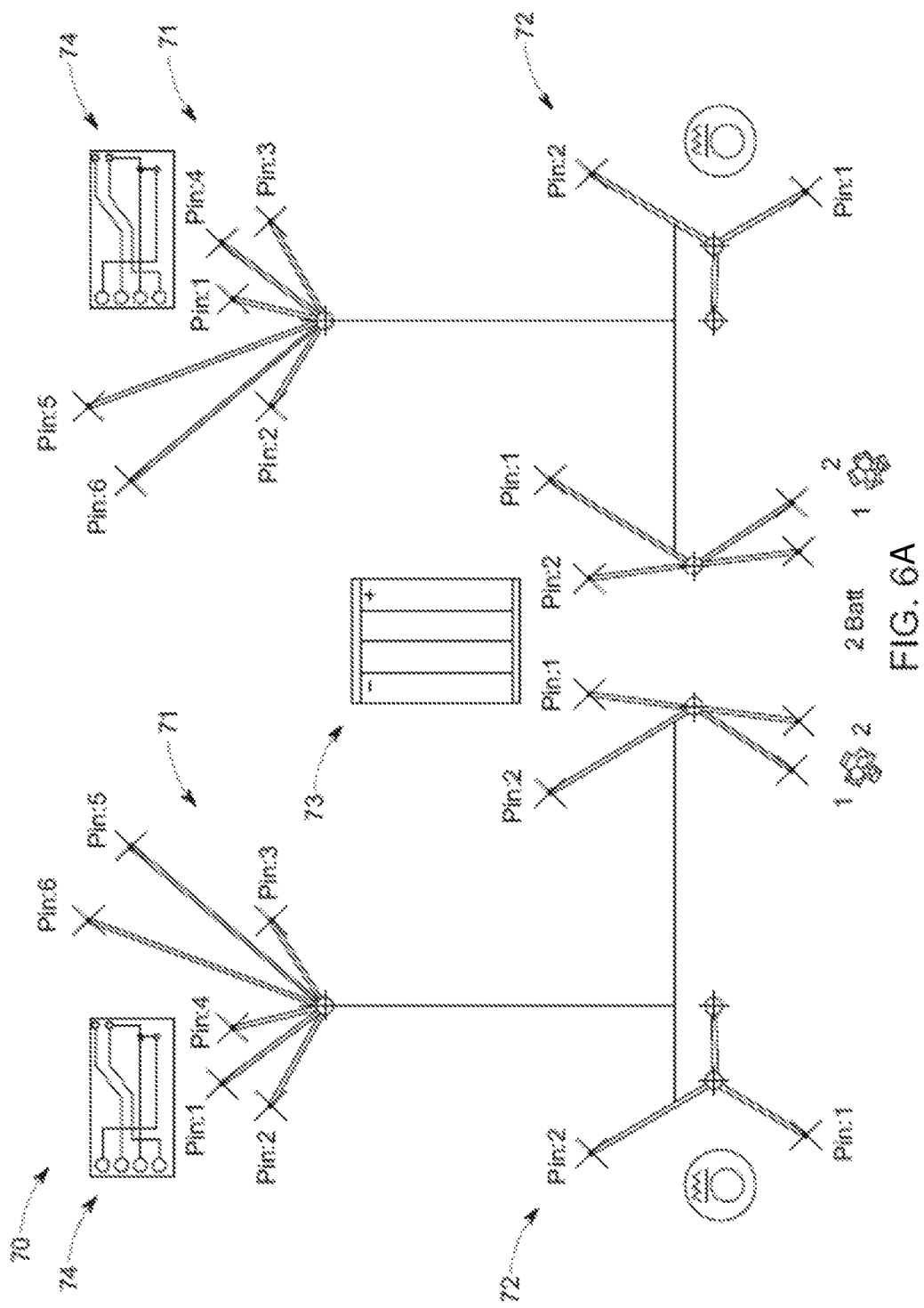
FIG. 6A illustrates wiring and electronics for a sensor activated pump mechanism.

As illustrated in FIG. 6A, the hand sanitizing station 10 includes at least one sensor activated pump mechanism 70. The sensor activated pump mechanism 70 includes a sensor device 71, an actuator 72, and an energy source 73. In some embodiments, the sensor device 71 is an infrared sensor. In some embodiments, the energy source 73 is a battery. In some embodiments, the energy source 73 is a rechargeable battery. In another embodiment, the energy source 73 is a nonmemory-type battery is selected from a group consisting of nickel-metal-hydride batteries or lithium ion batteries. The sensor device 71 can be connected to a circuit system 74 such as a circuit board, integrated circuit, or circuitry device. The actuator 72 can be any type of actuator. In some embodiments, the actuator 72 is an electric motor. In some embodiments, the circuit system 74 has a preset input that can switch the output of the energy source 73 to provide operational power to the actuator 72 when the sensor device 71 is triggered. In some embodiments, when the sensor activated pump mechanism 70 is engaged the viscous material contained within the dispensing chamber 40 is drawn through the feed conduit 43 and out the discharge nozzle 51.

Figure 6B:
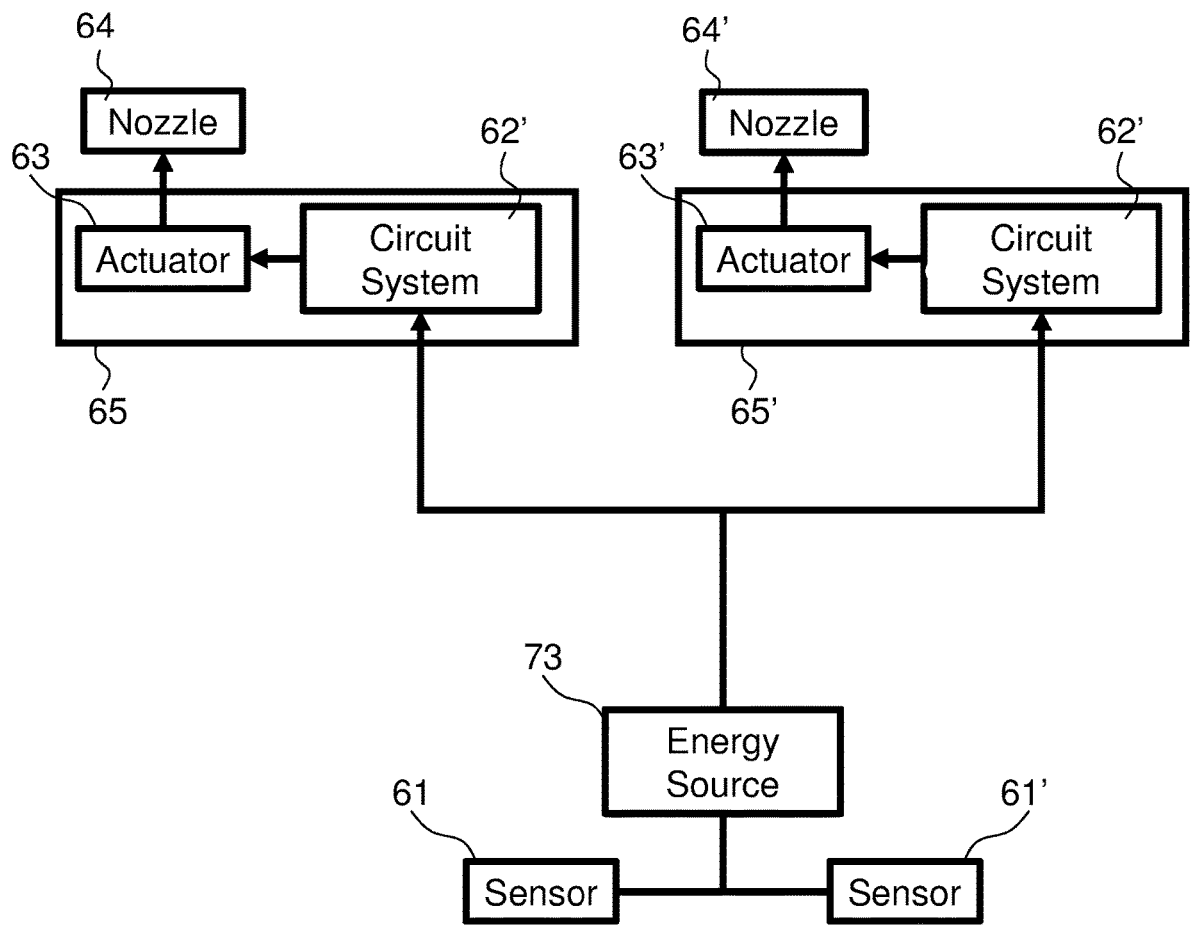
FIG. 6B illustrates a schematic diagram of the two chambered hand sanitizing station system.

As illustrated in FIG. 6B, in an aspect, the hand sanitizing station may include two sensor activated pump mechanisms 65, 65' and at least two sensors 61, 61'. The sensor activated pump mechanisms can be powered by a single energy source 73. The sensor activated pump mechanisms can be triggered by the actuator 63, 63' to dispense a predetermined quantity of viscous material.

Although this invention has been disclosed in the context of a certain preferred embodiment and examples, it will be understood by those skilled in the art that the present invention extends beyond the specifically disclosed embodiment to other alternative embodiments and/or uses of the invention and obvious modifications and equivalents thereof. Also, while several variations of the invention have been shown and described in detail, other modifications, which are within the scope of this invention, will be readily apparent to those of skill in the art based upon this disclosure. It is also contemplated that various combination or sub-combinations of the specific features and aspects of the embodiments or variations may be made and still fall within the scope of the invention. It should be understood that various features and aspects of the disclosed embodiment can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

The invention claimed is:

1. An apparatus for streamlined cleaning, drying, and sanitizing hands comprising:
    a base configured to dispense towels comprising a bottom wall, a back wall, at least one interior side wall, at least one exterior side wall, one front wall, and a dispenser with a base;
    wherein a space in a base of the dispenser at a bottom covered by the bottom wall includes a battery holder, switch, and a motor;
    two dispensing chambers configured to store a viscous material;
    wherein each dispensing chamber is connected to opposite sides of the base via at least a coupling conduit;
    a chamber cap and a compartment cover placed on top of each dispensing chamber, each chamber cap comprising a discharge nozzle placed on an edge of each chamber cap, and an opening for the viscous material to be poured into each dispensing chamber;
    at least one compartment cover, wherein the compartment cover is placed over the chamber cap covering the discharge nozzle, and wherein the compartment cover includes a refill cap opening and a refill cap;
    two sensor activated pump mechanisms each consisting of a sensor device connected to a circuit system, and an actuator; wherein the two sensor activated pump mechanisms are powered by a single energy source;
    wherein when the sensor device is triggered, the respective sensor activated pump mechanism is configured to draw a predetermined volume of viscous material through the conduit and out the discharge nozzle;
    and wherein the sensor activated pump mechanisms are powered by a single energy source, are configured to operate independently from one another, and are triggered by the actuator to dispense a predetermined quantity of viscous material onto an user's hand or hands allowing for streamlined cleaning, drying, and sanitizing of the user's hand or hands.

2. The apparatus of claim 1, wherein the viscous material is selected from the group consisting of soap, lotion, hand sanitizer, essential oil, foam, gel, shampoo, conditioner, topical medication, liquid baby powder, dye, hair mousse, toothpaste, mouthwash, liquid makeup, facial creams, sunscreen, detergent, and shaving cream.

3. The apparatus of claim 1, wherein each chamber cap is configured to form a seal at the top of each dispensing chamber for maintaining the viscous material within each dispensing chamber.

4. The apparatus of claim 1 wherein the sensor device is an infrared sensor.

5. The apparatus of claim 1, wherein the base is configured to store a plurality of towels.

6. The apparatus of claim 1, wherein each dispensing chamber is made from a material selected from the group consisting one of vinyl, plastic, plastic polymers, copper, pewter, and stainless steel.

7. The apparatus of claim 6, wherein the plastic polymers are selected from the group consisting one of low-density polyethylene, high-density polyethylene, polypropylene, polyvinyl chloride, polystyrene, nylon, polytetrafluoroethylene, and thermoplastic polyurethanes.

8. The apparatus of claim 1, wherein each dispensing chamber further comprise a back wall formed of a transparent material.

9. The apparatus of claim 1, wherein the front wall includes a cutout extending no more than 3 inches from the top of the front wall.

* * * * *